United States Patent [19]

Morganti

[11] Patent Number: 4,806,525

[45] Date of Patent: Feb. 21, 1989

[54] FORMULATION COMPRISING GELATIN AND GLYCINE FOR TREATING THE DRYNESS OF SKIN

[75] Inventor: Pier F. Morganti, Rome, Italy

[73] Assignee: Mavi S.r.l., Rome, Italy

[21] Appl. No.: 65,043

[22] Filed: Jun. 18, 1987

[51] Int. Cl.$^4$ .............................................. A61K 37/02
[52] U.S. Cl. ..................................... 514/21; 514/257; 514/306; 514/826; 514/844
[58] Field of Search ............... 514/844, 847, 257, 306, 514/826, 21

[56] References Cited

U.S. PATENT DOCUMENTS 4,590,069  5/1986  Deckner et al. ..................... 514/847
4,650,804  3/1987  Kitaura et al. ....................... 514/306

OTHER PUBLICATIONS

Susumu Tatsumi, Ph.D, *Pyrrolidonecarboxylic Acid*, vol. 87, Mar. 1972, p. 61–63.
Karl Laden, Ph.D., *Identification of a Natural Moisturizing Agent in Skin*, J. Soc. Cosmetic Chemistry, 18, 351–360, 5/27/67.
Blank, Ph.D, *Factors Which Influence the Water Content of the Stratum Corneum*, Journal of Investigative Dermatology.
J. D. Middleton, *The Mechanism of Water Binding in Stratum Corneum*, Brit. J. Derm., (1968), 80, p. 437–449.

*Primary Examiner*—John Kight
*Assistant Examiner*—Carlos Azpuru
*Attorney, Agent, or Firm*—Marshall & Melhorn

[57] ABSTRACT

A formulation comprised of soft gelatin and glycine in a proportion of about 3:1 to 2:1 by weight, to which can be added mineral oligoelements and vitamins, which, when administered orally, exerts in a relatively short time a moisturizing activity on skin suffering from dryness.

14 Claims, 1 Drawing Sheet

FORMULATION COMPRISING GELATIN AND GLYCINE FOR TREATING THE DRYNESS OF SKIN

The present invention relates to a composition for oral administration to humans for the treatment of skin dryness comprising a mixture of soft gelatin and glycine and to a method of using the composition to reduce the dryness of the skin.

BACKGROUND OF THE INVENTION

So-called "dry skin" is the first and the most obvious manifestation of a downward modification in the moisture content of the epidermis. It occurs more frequently during the cold season. But, it can be seen also in other periods of the year, for example following an extended and excessive exposure to solar rays (R. Jackson 27, 106 an B. A. Gilchrest, J. Soc. Cosmet. Chem. 32, 153).

According to published research, both the moisture content and the state of elasticity of the skin depend essentially upon the amount of water present at the level of the horny layer of the skin (stratum corneum). This is directly linked to a greater or lesser presence of Natural Moisturizing Factor (NMF). (J. Blank, J. Invest. Dermatol. 18 433–440 and K. Laden and R. Spitner, J. Soc. Cosmet. Chem. 18, 351).

NMF is a mixture of a series of amino-acids (containing about 12% of the sodium salt of 5-oxyproline) along with sugars.

The moisturizing activity effected by NMF would be basically due to this presence of the glutamic acid derivative, 5-oxyproline, which is currently better known as 2-pyrrolidone-carboxylic acid or by the abbreviation PCA (H. W. Speir and P. G. Pascher, Hautarzt, 7, 55, J. D. Middleton, Br. J. Dermat. 80, 437 and S. Tatsumi, Amer. Perf. 87,61).

PCA, transformed into glutamic acid by 5-oxyprolinase, takes part together with glyxine and cysteine in the metabolic cycles of glutathione (A. Meister "Metabolism and transport of glutathione and other glutamyl compounds" in "Functions of glutathione" A. Laron, S. Orrenius, A. Holmgren and B. Maunervik, Raven Press N.Y., page 1, 1983).

As is well known, glutathione is a tripeptide formed by elementary amino acids glycine, cysteine and glutamic acid. It is also known that, in the metabolic cycle, glutathione reaches the interior of the cells, rather than the intercellular tissue wherein the phenomena inherent to the moisturizing of the skin take place. It is consequently surprising that administering glycine associated with gelatin produces a highly favorable effect on the skin moisture, since, according to previous literature, the administration of glutamic acid, to which the presence of NMF is linked, could appear more promising to this end.

In the past, glycine (which is a known elementary amino acid) was used for the treatment of muscular dystrophy and it is known that an administration thereof orally has a favorable effect on the smooth mosculature.

Moreover, it is not known that an administration of gelatin alone could have a favorable influence on cutaneous moisturization.

Gelatin (which in the official pharmacopea is formally named "Gelatina F.U." or, according to the International name "Gelatinum"), is a known substance which is used, in particular, for the production of medicinal capsules.

In gelatin itself, among other things, a certain amount of glycine is present and it is a surprising fact that, while gelatin powder has no effect on the cutaneous moisture, the association thereof with additional glycine, in a determined proportion, makes it possible to obtain the desired effect upon cutaneous moisture.

OBJECTS OF THE INVENTION

Consequently, an object of the present invention is to provide a formulation for the treatment of skin dryness comprising a mixture of gelatin and glycine in proportions of from about 2:1 to 3:1 parts by weight and preferably a gelatin and glycine of about 2.5:1 parts by weight.

It is an object of the present invention to provide a composition for reducing dryness of the skin by oral administration, the composition comprising soft gelatin and intimately distributed in a homogenous way in the gelatin an effective dry skin reducing amount of glycine.

It is an object of the present invention to provide a method of reducing skin dryness, the method comprising the step of orally administering a composition comprising gelatin and glycine in a weight ratio of gelatin to glycine of about 2:1 to 3:1 to thereby reduce or eliminate skin dryness, the oral administration generally involving daily amounts of about 1000 mg. to 3000 mg. of gelatin and about 400 to 1200 mg. of glycine.

BRIEF DESCRIPTION OF THE DRAWINGS

The above and other objects will become apparent from the specification that follows, the appended claims, and the drawings, in which:

SUMMARY OF THE INVENTION

Figures 1, 2, 3:
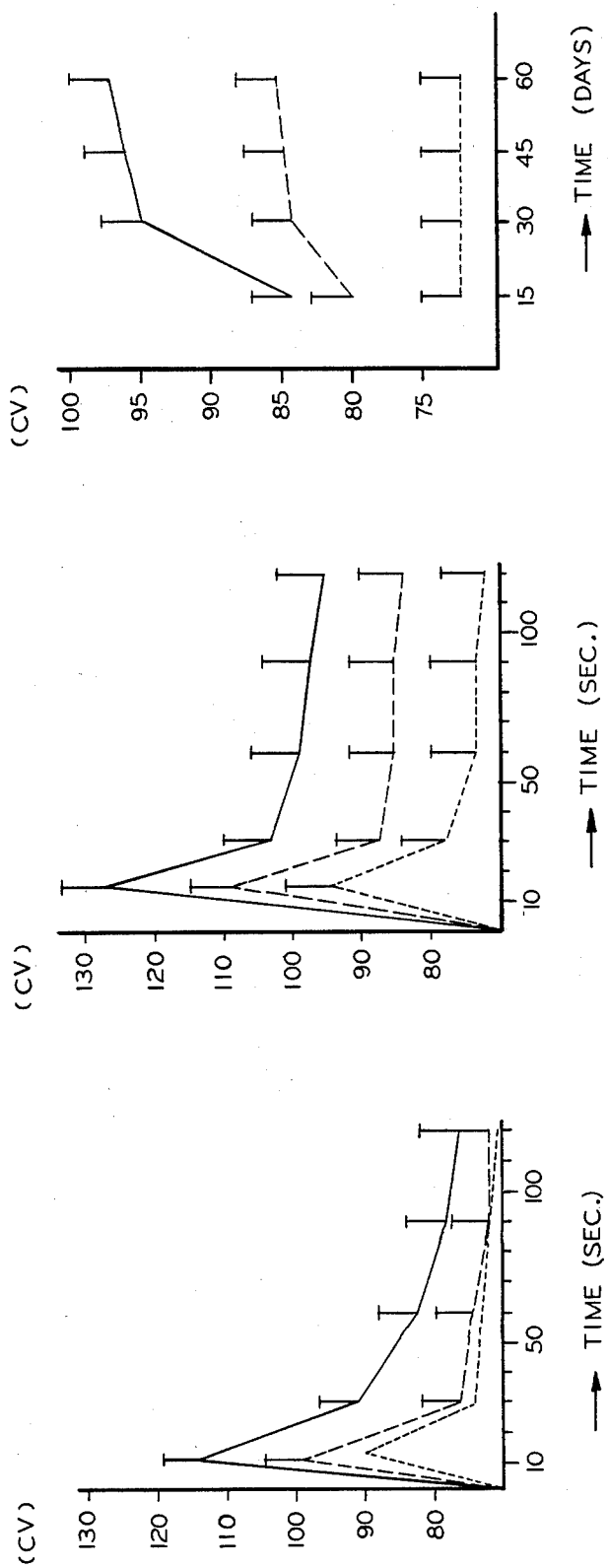
FIG. 1 shows the moisture holding capacity of human skin after oral administration of the unique soft gelatin/glycine composition of the present invention, the test corneometer values (cutaneous moisture being plotted against time, the composition being taken for 15 days.
FIG. 2 shows a graph comparing a gelatin/starch composition (FIG. 2) against the gelatin/glycine composition of FIG. 1.
FIG. 3 shows a graph similar to FIG. 1 showing a control in which there is no oral administration.

The present invention provides a composition for reducing dryness of the skin by oral administration, the composition comprising soft gelatin and an effective dry skin reducing amount of glycine.

The present invention also provides a method of reducing dryness of skin comprising the steps of orally administrating a composition comprising soft gelatin with a dry skin reducing amount of glycine intimately distributed in a homogenous way in the gelatin to thereby reduce dryness of the skin.

The weight ratio of gelatin to glycine is generally about 2:1 to 3:1 and preferably about 2.5:1 to 2.6:1.

In terms of daily dosage, the amount of gelatin is generally about 1000 mg. to 3000 mg. and preferably about 1800 mg. to 2200 mg. and the amount of glycine is generally about 400 to 1200 mg. and preferably about 600 to 100 mg.

DETAILED DESCRIPTION OF THE INVENTION

Part of the glycine may be substituted by small quantities of oligominerals and vitamins. This addition results in an improvement of the effects on dry skin. Capsules of so-called "soft" gelatin are used as containers for different active pharmaceutical principles. Such capsules of soft gelatin are usually hollow, in that they are intended to contain a medicinal product in the cavity. They may be used for these preparations of the present invention.

It is, however, also possible and preferable to use solid spherules. A cutaneous moisturization action has been found on administration of the formulation orally, in the form of soft spherules, formed b a method known as the Scherer method, (described, for example, in the U.S. Pat. Nos 2,318,718; 2,356,436; 2,333,433; 2,379,816; 2,378,817; and 2,451,141) or also by other methods.

By the term "soft solid gelatin spherules" a spherule free of cavity is intended, wherein the glycine is fused together to the gelatin components, such as to be intimately dispersed therein, rather than contained in a shell of gelatin as a separate phase. The methods for the preparation of solid spherules are known from the prior art.

As an example, the spherule can weigh 2.8 g., of which 2 g. is the amount of gelatin and 800 mg. is the amount of glycine.

The following examples illustrate the present invention:

EXAMPLE 1

Materials and Methods

Solid spherules of gelatin-glycine prepared according to a particular process, each formed by 500 mg. gelatin and 200 mg. glycine, were used.

Test of water absorption-ejection:

In order to evaluate the skin moisture of the test subject, measurements were taken from a previously determined area of the right forearm by the use of the Corneometer CM 420 and following the method of Tagami and coll. (H. Tagami et al, J. Invest. Dermatol. 78,425). Said method consists of applying 0.1 ml. distilled water on a skin surface of 2.5 sq.cm. (2). Ten seconds after application, the excess water is eliminated by absorbent paper and the first measurement is immediately effected. Measurement is repeated at 30, 60, 90 and 120 seconds.

The measurements were carried out by Corneometer CM 420, based on the principle of dielectric constants (K. Mosler, Parf. und Kosmetik 64,375).

The results obtained are referred to in FIGS. 1 and 2.

Evaluation of the Cutaneous Moisture on Human Skin

To 30 female volunteers between 30 and 40 years of age, all suffering from dry skin, spherules of gelatin-glycine (spherules A) and control spherules wherein glycine was substituted by starch (spherules B), were delivered following the double blind system. Neither the operator nor the subjects were able to identify the product considered as active.

The spherules were taken orally in a quantity of four spherules a day for a consecutive 60-day period between September and December.

Ten days before and continually during the treatment, the subjects did not use any cosmetic, with the exception of a detergent milk.

Fifteen female control subjects of the same average age made use only of the same detergent milk which was used in the morning as a cleanser.

Before beginning the treatment, at ten o'clock a.m., the moisture content and the ability of the skin to bind water (test of absorption-ejection) was evaluated "in vivo". The detergent milk had been used 1 hour previously.

The room where all measurements have been carried out was maintained at constant conditions of temperature and moisture (temp +18 C. Rel. Humidity 50%).

Once the test began, readings were taken on the 15th, 30th, 45th and 60th days. On such days, after effecting the direct control reading, the ability of the skin to bind water was also evaluated following the method of water absorption-ejection of Tagami. The values as obtained are found in Table 1 and in a graphic form in FIG. 3.

Test Summary

In FIG. 1 are shown the values of water absorption-ejection after an oral administration for 15 days of gelatin-glycine (average of 15 subjects per group).

In FIG. 2 are shown the values of water absorption-ejection after oral administration for 30 days of gelatin-glycine (average of 15 subjects per group).

In FIG. 3 is shown the evaluation of the cutaneous moisture after an oral administration of gelatin-glycine across the 60-day test period (average of 15 subject per group.

In Table 1 are shown the values of the evaluation of the cutaneous moisture after an oral administration of gelatin-glycine, as compared to the administration of gelatin-starch, and both as compared to controls (average of 15 subjects per each group).

Results and Comments

As can be seen from FIGS. 1 and 2, an oral administration of gelatin-glycine considerably increases the ability to bind water by human skin. Such an increase, which can already be noted after about a 15-day treatment by the oral route, reaches the highest values after 30 days, increasing by 40%. In fact, the values determined on the 60th day do not significantly differ from those after only a 30-day treatment (see FIG. 3 and Table 1).

It will be appreciated that the ability of the skin to retain water can be directly related to the amount of glycine present in the spherules.

A good improvement was found even in the individuals who took product B (control) comprised of gelatin and starch. As mentioned hereinbefore, gelatin is a protein of animal origin, the amino acid composition of which includes about 30% glycine.

The activity of gelatin-glycine with respect to cutaneous hydration can be even more clearly seen from FIG. 3 and Table 1. Improvement in the cutaneous horny layer moisture can be noted, as detected and demonstrated by means of a Corneometer CM 420. The moisture increases by about 20% after only the first 30 days of treatment, which improvement continues to be maintained during the following days of oral therapy.

FIG. 3 and Table 1 also demonstrate the tendency of gelatin to improve the cutaneous moisture in the treated individuals. Probably glycine, through the glutathione cycle, increases significantly the production of cellular PCA which can be detected at the level of the horny layer.

EXAMPLE 2

Experimentation was carried out in the same fashion and using the same apparatus as described in Example 1.

Materials and Methods

Soft gelatin scherer capsules were used, having the following compositions:

| CAPSULE "A" | |
|---|---|
| Beeswax | 30 mg. |
| Soy lecithin | 34 mg. |
| Vegetable oil | 310 mg. |
| Starch | 200 mg. |
| Gelatin | 250 mg. |
| Shell | |
| Gelatin | 186 mg. |

CAPSULE "B"

Starch was replaced by a similar amount of glutamic acid.

CAPSULE "C"

Starch was replaced by a similar amount of gelatin.

CAPSULE "D"

Gelatin was replaced by starch and the amount of starch indicated in Capsule "A" was replaced by a similar amount of glycine.

CAPSULE "E"

Starch was replaced by glycine.

CAPSULE "F"

Starch was replaced by 150 mg. glycine, plus oligoelements (ferrous lactate, manganese oxide, copper lactate, and tri-calcium phosphate in such amount as to provide 3 mg. $Fe^{++}$, 0.5 mg. $Mn^{++}$, 0.6 mg. $Cu^{++}$, 50 mg. $Ca^{++}$) also added were 10 mg. of Vitamin C and 0.4 mg. of Vitamin B-6.

Evaluation of Affects Upon the Hydration of Human Skin

Sixty female volunteers between 35 and 43 years of age and affected by dry skin, were divided into 6 lots of 10 individuals. Each lot of individuals received randomly from the experimentor a specific group of capsules sufficient for two months of treatment, 240 capsules per individual. The capsules, divided into 6 groups were distinguished with letters A to F, as noted:

A—Gelatin and Starch (control)
B—Gelatin and Gutamic acid
C—Gelatin alone
D—Glycine and Starch
E—Gelatin and Glycine
F—Gelatin and Oligoelements and Vitamins and Glycine Neither the operator nor the subjects were able to identify the product.

The capsules were administered orally in a dose of 4 per day for 60 consecutive days.

The 10 individuals receiving the capsules indicated as "A" have been considered as controls.

As seen in Tables 2, 3, 4 and 5 no positive results have been obtained with the capsules indicated by letters A, B. C. and D.

Not gelatin alone nor with glutamic acid added, nor glycine along (without gelatin) is capable of improving the moisturization degree of human skin by the method used.

When gelatin is added to glycine (Capsule E) a 12% increase in cutaneous moisturization is obtained after 15 days and a 30% increase is obtained after 30 to 45 days of oral treatment (Table 6).

If the glycine amount is reduced from 200 mg. to 50 mg., however, with an addition of oligoelements (iron, manganese, copper, and calcium) and specific vitamins (Vitamin C and Vitamin B-6) an even greater increase is verified. This increase is 30% after 15 days and 40% after 30 to 45 days of treatment (Table 7).

TABLE 1

Evaluation of the cutaneous moisturization after oral administration of gelatin/glycine (average of 15 persons per group).

| | CONTROLS (no oral administration) days | | | | | SPHERULES B (GELATIN/STARCH) days | | | | | SPHERULES A (GELATIN/GLYCINE) days | | | |
|---|---|---|---|---|---|---|---|---|---|---|---|---|---|---|
| PA-TIENT | 15 | 30 | 45 | 60 | PA-TIENT | 15 | 30 | 45 | 60 | PA-TIENT | 15 | 30 | 45 | 60 |
| 1 | 73 | 69 | 76 | 75 | 16 | 79 | 85 | 84 | 85 | 31 | 85 | 94 | 94 | 96 |
| 2 | 70 | 74 | 75 | 73 | 17 | 78 | 84 | 82 | 83 | 32 | 87 | 98 | 96 | 99 |
| 3 | 76 | 70 | 77 | 76 | 18 | 83 | 88 | 88 | 87 | 33 | 83 | 92 | 98 | 100 |
| 4 | 75 | 72 | 70 | 77 | 19 | 80 | 87 | 80 | 86 | 34 | 88 | 98 | 96 | 96 |
| 5 | 73 | 77 | 75 | 76 | 20 | 84 | 83 | 84 | 89 | 35 | 82 | 95 | 98 | 100 |
| 6 | 71 | 68 | 73 | 70 | 21 | 82 | 84 | 87 | 88 | 36 | 84 | 98 | 100 | 105 |
| 7 | 70 | 74 | 75 | 73 | 22 | 80 | 85 | 85 | 82 | 37 | 82 | 94 | 98 | 105 |
| 8 | 68 | 73 | 72 | 77 | 23 | 78 | 82 | 83 | 85 | 38 | 84 | 99 | 100 | 99 |
| 9 | 74 | 70 | 75 | 78 | 24 | 82 | 84 | 87 | 82 | 39 | 88 | 98 | 100 | 105 |
| 10 | 69 | 76 | 74 | 72 | 25 | 82 | 86 | 85 | 86 | 40 | 83 | 94 | 96 | 98 |
| 11 | 77 | 71 | 76 | 75 | 26 | 84 | 84 | 87 | 89 | 41 | 87 | 98 | 94 | 96 |
| 12 | 72 | 77 | 70 | 72 | 27 | 81 | 80 | 83 | 84 | 42 | 82 | 93 | 97 | 97 |
| 13 | 70 | 75 | 71 | 76 | 28 | 81 | 80 | 82 | 84 | 43 | 86 | 94 | 99 | 105 |
| 14 | 75 | 68 | 69 | 71 | 29 | 80 | 81 | 83 | 87 | 44 | 86 | 93 | 98 | 100 |
| 15 | 70 | 73 | 77 | 78 | 30 | 81 | 82 | 88 | 85 | 45 | 86 | 98 | 100 | 95 |
| Average | 72,2 | 72,4 | 73,7 | 74,6 | Average | 81 | 83,7 | 84,5 | 85,5 | Average | 84,8 | 95,7 | 97,6 | 99,7 |

TABLE 2

| | CAPSULE "A" (Gelatin & Starch) | | |
|---|---|---|---|
| | | Control | |
| Patient | 15 | 30 | 45 |
| 1 | 78 | 74 | 76 |

TABLE 2-continued

CAPSULE "A" (Gelatin & Starch)

| Patient | Control 15 | 30 | 45 |
|---|---|---|---|
| 2 | 72 | 76 | 78 |
| 3 | 75 | 75 | 78 |
| 4 | 77 | 73 | 75 |
| 5 | 74 | 77 | 73 |
| 6 | 72 | 74 | 76 |
| 7 | 76 | 78 | 73 |
| 8 | 78 | 74 | 72 |
| 9 | 73 | 75 | 77 |
| 10 | 75 | 72 | 76 |
| average | 75.1 | 75.4 | 75.1 |
| variation | 4.09 | 4.44 | 5.69 |
| standard deviation | 2.02 | 2.11 | 2.39 |

TABLE 3

Capsule "B" (Gelatin + Glutamic Acid)

| Patient | Control 15 | 30 | 45 |
|---|---|---|---|
| 11 | 78 | 78 | 77 |
| 12 | 75 | 76 | 75 |
| 13 | 73 | 79 | 76 |
| 14 | 75 | 77 | 74 |
| 15 | 76 | 74 | 73 |
| 16 | 74 | 77 | 75 |
| 17 | 78 | 75 | 76 |
| 18 | 76 | 78 | 74 |
| 19 | 73 | 77 | 74 |
| 20 | 73 | 78 | 74 |
| average | 75.1 | 76.9 | 74.8 |
| variation | 3.29 | 2.09 | 1.36 |
| standard deviation | 1.81 | 1.45 | 1.17 |

TABLE 4

Capsule "C" (Gelatin)

| Patient | Control 15 | 30 | 45 |
|---|---|---|---|
| 21 | 76 | 78 | 75 |
| 22 | 73 | 73 | 76 |
| 23 | 74 | 76 | 73 |
| 24 | 75 | 74 | 76 |
| 25 | 78 | 76 | 75 |
| 26 | 72 | 74 | 73 |
| 27 | 72 | 73 | 74 |
| 28 | 73 | 76 | 75 |
| 29 | 75 | 75 | 76 |
| 30 | 77 | 76 | 75 |
| average | 74.5 | 75.1 | 74.8 |
| variation | 3.85 | 2.29 | 1.16 |
| standard deviation | 1.96 | 1.51 | 1.08 |

TABLE 5

Capsule "D" (Glycine + Starch)

| Patient | Control 15 | 30 | 45 |
|---|---|---|---|
| 31 | 74 | 76 | 79 |
| 32 | 77 | 76 | 75 |
| 33 | 73 | 72 | 75 |
| 34 | 78 | 79 | 78 |
| 35 | 75 | 77 | 76 |
| 36 | 72 | 73 | 74 |
| 37 | 76 | 74 | 70 |
| 38 | 75 | 75 | 73 |
| 39 | 78 | 78 | 75 |
| 40 | 73 | 74 | 76 |
| average | 75.1 | 75.4 | 75.1 |
| variation | 4.09 | 4.44 | 5.69 |
| standard deviation | 2.02 | 2.11 | 2.39 |

TABLE 6

Capsule "E" (Gelatin + Glycine)

| Patient | Control 15 | 30 | 45 |
|---|---|---|---|
| 51 | 85 | 99 | 96 |
| 52 | 84 | 97 | 98 |
| 53 | 86 | 89 | 91 |
| 54 | 83 | 92 | 93 |
| 55 | 87 | 97 | 96 |
| 56 | 84 | 98 | 99 |
| 57 | 86 | 95 | 95 |
| 58 | 82 | 93 | 98 |
| 59 | 84 | 90 | 95 |
| 60 | 87 | 97 | 99 |
| average | 84.8 | 94.7 | 96.0 |
| variation | 2.56 | 11.01 | 6.20 |
| standard deviation | 1.60 | 3.32 | 2.49 |

TABLE 7

Capsule "F" (Gelatin + Oligoelements + Vitamins + Clycine)

| Patient | Control 15 | 30 | 45 |
|---|---|---|---|
| 41 | 91 | 105 | 105 |
| 42 | 89 | 107 | 106 |
| 43 | 90 | 100 | 104 |
| 44 | 92 | 104 | 105 |
| 45 | 94 | 110 | 109 |
| 46 | 92 | 100 | 106 |
| 47 | 94 | 103 | 104 |
| 48 | 96 | 110 | 108 |
| 49 | 90 | 100 | 110 |
| 50 | 93 | 107 | 110 |
| average | 92.1 | 104.6 | 106.7 |
| variation | 4.29 | 13.64 | 5.01 |
| standard deviation | 2.07 | 3.69 | 2.24 |

A statistical analysis of the results obtained provides the following comparison table of the theoretical mean values of the degree of cutaneous moisturization obtained after administering the different types of capsules.

TABLE 8

| | Theoretical Mean Values | | |
|---|---|---|---|
| | 15 days | 30 days | 45 days |
| CAPSULE A | 74.87 | 75.07 | 75.27 |
| CAPSULE B | 75.75 | 75.60 | 75.45 |
| CAPSULE C | 74.65 | 74.80 | 74.95 |
| CAPSULE D | 75.20 | 75.20 | 75.20 |
| CAPSULE E | 86.10 | 92.10 | 98.10 |
| CAPSULE F | 93.83 | 101.13 | 108.43 |

The data obtained in the second experiment indicates that the gelatin used in the capsules or spherules as a "carrier" of glycine is able to make glycine immediately available as an essential and usable amino acid for collagen, and probably also elastin, formation. The increase in cutaneous moisturization observed after oral administration of gelatin-glycine is further increased by 10–15% when the glycine is enriched with oligoelements ($Fe^{++}$, $Cu^{++}$, $Zn^{++}$ and $Ca^{++}$) in the form of normally tolerable salts such as iron gluecont, iron sulfate, iron chloride and similar copper zinc and calcium salts which are considered as cofactors necessary both for the metabolic balance of and the building of, internal and external bonds of the collagen and elastin molecules. Vitamin C acts as cofactor in the hydroxylation process of proline and lysine radicals, and the Vitamin B-6 acts as an enzyme (as pyridoxal phosphate) in the oxidative deamination reaction of the free amino group of lysine and oxylysine.

From the data and observations, it appears that the combination of gelatin-glycine acts by means of two different biological mechanisms. The combination promotes collagen synthesis by raising the deep cutaneous moisturization and activates one or more enzyme systems which are required for a continuous cutaneous production of sodium PCA, which is partly responsible for surface moisturizing activity.

What is claimed is:

1. A pharmaceutical formulation for the treatment of skin dryness, characterized by the content, as active substances, of a composition of soft gelatin and glycine in a proportion of about 2:1 to 3:1 parts by weight.

2. A formulation, according to claim 1, wherein the proportion by weight of gelatin and glycine is about 4:2.5.

3. A formulation, according to claim 1, wherein there is a mineral oligoelement selected from a member of the group consisting of $Fe^{++}$, $Mn^{++}$, $Cu^{++}$, $Ca^{++}$ or mixtures thereof.

4. A formulation, according to claim 1, comprising: 436 mg. gelatin, 150 g. glycine, 3 mg. $Fe^{++}$, 0.5 mg. $Mn^{++}$, 0.6 mg. $Cu^{++}$, 40 mg. $Ca^{++}$, 10 mg. vitamin C and 0.4 mg. vitamin B-6.

5. Use of a composition comprising gelatin and glycine in a proportion 2:1 to 3:1 by weight, wherein a minor part of the amount of glycine can be replaced by mineral oligoelements and vitamins, for the manufacture of a product for treatment of skin dryness.

6. A formulation as described in claim 1 in which there is a vitamin.

7. A formulation as defined in claim 5 in which the vitamin is vitamin C or vitamin B-6, or mixtures thereof.

8. A composition for reducing dryness of the skin by oral administration, the composition comprising soft gelatin and an effective dry skin reducing amount of glycine.

9. A composition as defined in claim 7 in which the weight ratio of gelatin to glycine is about 2:1 to 3:1.

10. Composition as defined in claim 7 in which the weight ratio of gelatin to glycine is about 2.5:1.

11. A method of reducing dryness of skin comprising the step of:
   orally administrating a composition comprising soft gelatin and dry skin reducing amount of glycine intimately distributed in a homogenous way in the gelatin to thereby reduce dryness of the skin.

12. A method as defined in claim 10 in which the composition is taken orally about four times per day.

13. A method as defined in claim 10 in which the daily amount of soft gelatin is about 2000 mg. and the daily amount of glycine is about 800 mg.

14. A method as defined in claim 10 in which the daily amount of gelatin is about 1000 to 3000 mg. and the daily amount of glycine is about 400 to 1200 mg.

* * * * *